United States Patent [19]
Linder et al.

[11] 3,957,055
[45] May 18, 1976

[54] CATHETER GUIDE

[76] Inventors: Gerald S. Linder, 16693 Charmel Lane, Pacific Palisades, Calif. 90272; Harry Zimmerman, 12941 La Maida St., Sherman Oaks, Calif. 91423

[22] Filed: Sept. 23, 1974

[21] Appl. No.: 508,173

[52] U.S. Cl. .............................. 128/351; 128/341
[51] Int. Cl.² .......................................... A61M 25/00
[58] Field of Search ............ 128/351, 350 R, 349 R, 128/348, 341, 343, 4–8

[56] References Cited
UNITED STATES PATENTS

| | | | |
|---|---|---|---|
| 229,633 | 7/1880 | Pfarre | 128/341 |
| 2,221,138 | 11/1940 | Hendrickson | 128/349 R X |
| 2,541,402 | 2/1951 | Caine | 128/351 |
| 3,460,541 | 8/1969 | Doherty | 128/351 |
| 3,754,554 | 8/1973 | Felbarg | 128/351 |

OTHER PUBLICATIONS

Jour. Amer. Soc. Anesthesiologists, Inc. Mar.–Apr. 1968, Vol. 29, No. 2, p. 385.

*Primary Examiner*—Dalton L. Truluck
*Attorney, Agent, or Firm*—Arthur Decker; B. F. Spencer

[57] ABSTRACT

Disclosed is a guide in stylet form for aiding the insertion of catheters into, for instance, mucous canals of the living body for withdrawal of fluid from a cavity thereof, characterized by a core of solid, flexible metal completely encased in a self-lubricating material and an adjustable stop which also may be used as a grip for manipulation of the guide and an anchor for forming a handle by an end of the guide.

4 Claims, 5 Drawing Figures

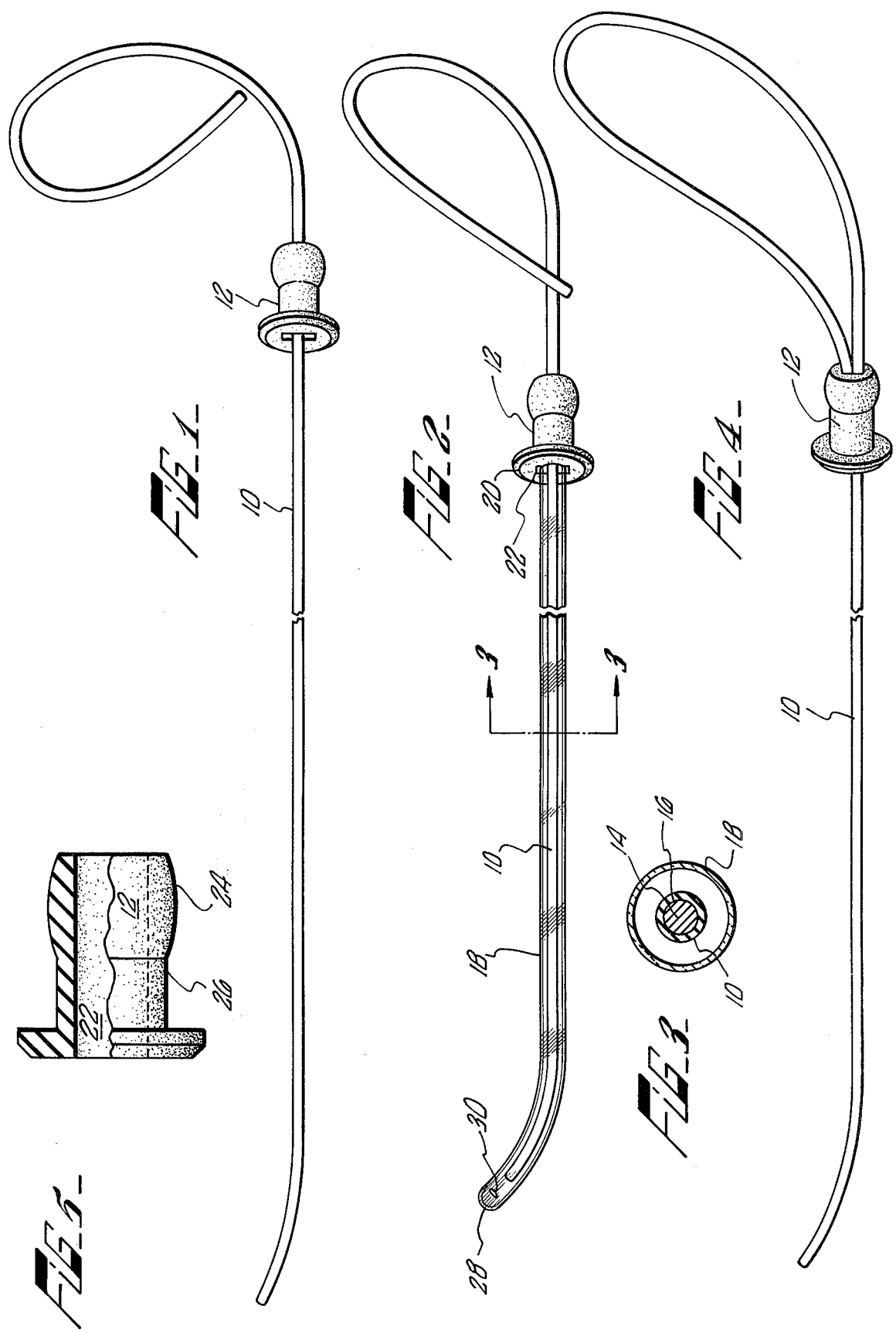

CATHETER GUIDE

BACKGROUND OF THE INVENTION

A sufficient variety of stylets has been used to facilitate intubation of endotracheal tubes to enable the stipulation of ideal characteristics for this type of surgical tool: safety to the patient by avoiding risk of both mechanical injury as well as infection of mucosal tissue, flexibility so that adaptation to body contour may be accomplished without undue strain or waste of time, self-lubricating during both insertion and withdrawal from the catheter, easily manipulated by the operator, sterilizable (by heat, cold or gas) without special provision and durable to provide indefinite reuse but nevertheless sufficiently economical to justify discard in appropriate circumstances.

SUMMARY OF THE INVENTION

This invention, in its preferred embodiment, comprises a catheter guide in the general form of a stylet, and possessing the aforementioned desirable characteristics, some to an extent not found in any guide previously divulged to the medical field. Briefly, it comprises a metallic core of solid wire of material and gauge appropriate and sufficient, respectively, to maintain its configuration indefinitely after shaping and to retain stiffness suitable for its use, completely coated, so as to be sealed hermetically, with polyolefin or the like, and equipped with a stop positionable along its length where desired by the surgeon. The guide may be made in a range of thicknesses and lengths appropriate for cooperation with all endotracheal catheters, whether the patient is a large adult or a newborn.

DESCRIPTION OF THE DRAWINGS

FIG. 1 depicts the catheter guide of the present invention with one end bent to form a handle;

FIG. 2 shows one end of the guide inserted into a catheter of clear plastic;

FIG. 3 is a cross-section taken along line 3—3 of FIG. 2;

FIG. 4 shows how the free or other end of the guide handle may be inserted into its stop; and FIG. 5 presents the stop in longitudinal cross-section.

DESCRIPTION OF THE PREFERRED EMBODIMENT

In FIG. 1, the preferred form for the present invention comprises stylet 10 on which is mounted stop 12.

Stylet 10 is shown as in the form of an elongated member which, although sufficiently flexible to be bent easily into a retained shape by the hands, is of a higher degree of rigidity than the usual plastic or rubber catheter. A number six to fourteen copper wire has been found quite suitable to act as core 14 of stylet 10 (see the cross-section, FIG. 3); this is coated completely, including the ends thereof, by sheath 16.

It may be well to point out here that, in order to establish a material for sheath 16 which would contribute the aforementioned desirable attributes, considerable experimentation among a wide variety of natural and synthetic compounds was necessary. Various rubbers, in general, were too easily damaged by repeated handling, Teflon (TM Dupont) posed great difficulty in forming a protective tip and also cracked too readily, peeled and scraped off the surface of stylet 10, and polyethylene was characterized by a variety of drawbacks. The material which was discovered to provide a preferred and final choice was polyolefin and, after application and extensive testing, was recognized as most nearly fulfilling the listed requirements.

With regard to the application of sheath 16 of polyolefin to core 14, any of the following processes are considered practical:

1. puddling at a temperature between 250° and 275° F, approximately, in melted polyolefin so that core 14 is immersed completely, including its ends, thereafter removing from the melt and permitting it to air dry;
2. spraying molten polyolefin on core 14 such that the latter is thoroughly covered, thereafter permitting it to air dry; and
3. molding in dies by compressing molten polyolefin around core 14.

Also exhibited by FIGS. 1 and 2, as well as by FIG. 4, are various configurations which may be formed at the other end of stylet 10 to provide a handle shaped with regard to use as a catheter guide and for comfort in operating the guide by hand. Additionally, FIG. 2 shows how one end of stylet 10 is inserted into catheter 18, which may be of soft, pliable plastic or rubber approximately 1/16 inch thickness of wall and about ¼inch in outside diameter, as appropriate for the mucous canal, and having rounded tip 28 and opening 30 close thereto, and all three of these figures illustrate the preferred form of stop 12 mounted on stylet 10.

In particular, stop 12 may be positioned along stylet 10 to conform to the length of catheter 18 such that the latter's open end will butt against shoulder 20 of the former (FIG. 2). In order that catheter 18 not enter inadvertently into and bind in stop 12, access through stop 12 is by way of rectangular slot or bore 22 (FIGS. 2, 5) having a width somewhat less than the outer diameter of the usual catheter. Further, to provide a good grip for the fingers, the other or rear end of stop 12 forms bulge 24 of diameter exceeding central body 26 into which, if desired, the other end of stylet 10 may be inserted (see FIG. 4). Preferably, stop 12 is fabricated of tough synthetic rubber or the like.

Briefly with regard to its use, to facilitate intubation, disposable endotracheal tubes should be cut to approximate length prior to insertion of the guide, and their connectors (as supplied, usually of plastic and having rather sharp edges) be installed after the tube has been inserted and stylet 10 has been withdrawn.

It should be understood that this invention is not restricted to any dimensions or materials specifically suggested or shown but is capable of other configurations without substantial departure from its essence; it follows that such variations are contemplated as within its scope.

What is claimed is:

1. A catheter guide in stylet form adapted for insertion into and withdrawal from a catheter comprising in combination:
   a. a wire of substantially uniform diameter composed of material sufficiently flexible to be configured by the hands into a desired shape, said wire having enough rigidity to maintain its shape indefinitely after configuration, the length of said wire between its ends being longer than the catheter into which it is to be used;
   b. a coating of polymer material, as, for example, polyolefin, securely attached to the surface of said wire including both ends thereof for completely enclosing and hermetically sealing said wire, said polymer coating possessing a pliable characteristic to accommodate the desired bending of said wire without separation from said wire and without rupture of the hermetic seal, said polymer coating having a smooth, self-lubricating surface to reduce friction during the insertion into and withdrawal of the coated wire from the catheter; and c. an adjustable stop of resilient material having a shoulder portion and a rear surface, said stop further having a central bore extending therethrough between the shoulder portion and the rear surface, said bore being of a size at the rear surface opening to receive at least two diameters of said coated wire said stop being slideably mounted on said coated wire for establishing the depth of penetration of one end of said coated wire into the catheter by the abutment of the shoulder portion of said stop against the open end of the catheter, the other end of said coated wire being adapted for insertion into the said opening at the rear surface of said stop for forming a handle.

2. The catheter guide as defined by claim 1 wherein said polymer coating comprises a non-elastomeric polymer having a coefficient of friction substantially less than that of rubber.

3. The catheter guide as defined by claim 2 wherein said wire of substantially uniform diameter is composed of solid metal, and the central bore through said adjustable stop is of rectangular cross section.

4. The catheter guide as defined by claim 3 wherein the central rectangular bore through said adjustable stop forms an anchor for the other end of said coated wire.

* * * * *